United States Patent
Holman et al.

(10) Patent No.: US 9,138,391 B2
(45) Date of Patent: Sep. 22, 2015

(54) NAIL POLISH REMOVER COMPRISING N-BUTYL ACETATE

(75) Inventors: Dianne Holman, Okemos, MI (US); Peter K. Rossman, Chicago, IL (US)

(73) Assignee: Working Bugs, LLC, East Lansing, MI (US)

( * ) Notice: Subject to any disclaimer, the term of this patent is extended or adjusted under 35 U.S.C. 154(b) by 0 days.

(21) Appl. No.: 14/239,579

(22) PCT Filed: Aug. 23, 2012

(86) PCT No.: PCT/US2012/052062
§ 371 (c)(1),
(2), (4) Date: May 2, 2014

(87) PCT Pub. No.: WO2013/028862
PCT Pub. Date: Feb. 28, 2013

(65) Prior Publication Data
US 2014/0315773 A1    Oct. 23, 2014

Related U.S. Application Data

(60) Provisional application No. 61/575,675, filed on Aug. 25, 2011.

(51) Int. Cl.
*C11D 3/43* (2006.01)
*A61K 8/37* (2006.01)
*A61Q 3/04* (2006.01)
*A61K 8/34* (2006.01)

(52) U.S. Cl.
CPC ... *A61K 8/37* (2013.01); *A61K 8/34* (2013.01); *A61Q 3/04* (2013.01)

(58) Field of Classification Search
CPC ........ C11D 3/201; C11D 3/2093; C11D 3/43; C11D 7/261; C11D 7/266; C11D 7/5004; C11D 7/5077
See application file for complete search history.

(56) References Cited

U.S. PATENT DOCUMENTS

| | | | |
|---|---|---|---|
| 2,393,864 A | 1/1946 | Francisco | |
| 2,825,696 A | 3/1958 | Zabban et al. | |
| 2,971,920 A | 2/1961 | Wurmbock et al. | |
| 3,150,048 A | 9/1964 | Hollub et al. | |
| 4,735,798 A * | 4/1988 | Bernstein | 424/61 |
| 5,063,049 A | 11/1991 | Billings | |
| 5,582,333 A | 12/1996 | Bennett | |
| 5,961,731 A * | 10/1999 | Cooper-Trotter | 134/6 |
| 6,028,040 A | 2/2000 | Jarema | |
| 6,093,410 A * | 7/2000 | Peffly et al. | 424/401 |
| 6,187,299 B1 * | 2/2001 | Wimmer et al. | 424/61 |
| 6,344,190 B1 | 2/2002 | Nair et al. | |
| 6,361,785 B1 | 3/2002 | Nair et al. | |
| 6,630,431 B2 | 10/2003 | Berglund | |
| 6,841,523 B1 * | 1/2005 | Holtz | 510/118 |
| 7,341,747 B2 | 3/2008 | Nair | |
| 2003/0195775 A1 * | 10/2003 | Hampton et al. | 705/3 |
| 2008/0153736 A1 | 6/2008 | Elder et al. | |

FOREIGN PATENT DOCUMENTS

WO    2011011304    1/2011

OTHER PUBLICATIONS

Notification of Transmittal of the International Search Report and the Written Opinion dated Oct. 17, 2012.

Shane, Devon, Sarah Diefendorf, Susan Blachman, Lisa fu, My tong, and Vicki Vasquez, "Mapping the Nail Care Industry: Personal Care Industry Information and Profiles of Leading Cosmetics, Beauty Store, and Nail Care Product Companies," Dominican University of California and California Healthy Nail Salon Collaborative, Mar. 2010; http://www.cahealthynailsalons.org/wp-content/uploads/2010/07/MappingTheNailIndustry_Final.pdf.

Canadian Centre for Occupational Health and Safety. "Health Effects of Acetone" Accessed Aug. 10, 2011.

* cited by examiner

*Primary Examiner* — Charles Boyer

(74) *Attorney, Agent, or Firm* — Butzel Long

(57) ABSTRACT

A nail polish remover that is safer and more environmentally friendly than conventional acetone-based and petrochemical-based nail polish removers containing a mixture of water and at least one lower alkyl acetate, and an amount of an emulsifier that is sufficient to emulsify the alkyl acetate to prevent phase separation of the mixture. Exemplary compositions include, as the lower alkyl acetate, n-butyl acetate in an amount of from 10% to 60% by volume, ethanol, as the emulsifier, in an amount of from 0 to 20% by volume, and the balance being water.

8 Claims, No Drawings

NAIL POLISH REMOVER COMPRISING N-BUTYL ACETATE

CROSS-REFERENCE TO RELATED APPLICATIONS

This application claims the benefit of PCT Application No. PCT/US2012/052062 filed Aug. 23, 2012 and U.S. Provisional Application No. 61/575,675 filed Aug. 25, 2011, which are hereby incorporated by reference in their entireties.

FIELD OF THE DISCLOSURE

This disclosure relates to safer and more environmentally friendly nail polish removers than acetone-based and petrochemical-based nail polish removers.

DESCRIPTION OF PRIOR ART

The most prevalent chemical nail polish removers on today's market contain acetone, a volatile organic compound (VOC). These nail polish removers work by the user absorbing a small amount of the liquid onto a sponge or other absorbent material, and rubbing the nail until the nail polish is removed. The absorbent material is then disposed of, and any remaining acetone evaporates into the atmosphere.

While acetone is an effective nail polish remover, it has its drawbacks. The vapors in acetone-based nail polish remover, like other harmful VOC's, can irritate the throat and sinus passages. At higher concentrations, harmful VOC's can cause dizziness, eye irritation, nausea, and possibly unconsciousness (CCOHS, 2011).

Conventional acetone production involves the reaction of benzene in the presence of catalysts, and/or the use of other potentially harmful chemicals such as sulfuric acid. (ICIS, 2011). Conventional acetone production also uses chemicals derived from petrochemical feedstocks, which will become scarce in the future.

A new market for bio-based nail polish removers has emerged in the past decade. In 2008, the natural and organic personal care products market was valued at $465 million, up 35% since 2005 (Shane and Diefendorf, 2010). These removers are less toxic and less harmful to the environment than acetone- and petrochemical-based products.

U.S. Pat. No. 6,841,523 addresses the need for a nail polish remover having reduced environmental impact by employing a combination of methyl acetate, a glycol ether coupling agent, and a stabilizer.

SUMMARY OF THE DISCLOSURE

Described herein is a bio-based nail polish remover composition which comprises a mixture of water, a lower alkyl acetate and an amount of an emulsifier sufficient to emulsify the alkyl acetate to prevent phase separation of the mixture. In certain embodiments, the emulsifier is an alcohol containing 2 to 4 carbon atoms. In certain embodiments, the alkyl moiety or group of the lower alkyl acetate contains 1 to 5 carbon atoms. In certain embodiments, the lower alkyl acetate is n-butyl acetate. In certain embodiments, the lower alkyl acetate is a mixture of a butyl acetate and an amyl acetate. In certain embodiments, the alkyl acetate is isoamyl acetate. In certain embodiments, the alcohol is ethanol. In certain embodiments, the lower alkyl acetate is n-butyl acetate (NBuAc) in an amount by volume of 10% to 20%, the alcohol is ethanol in an amount by volume of 10% to 60%, and the balance is water. The solution remains clear upon standing over time. In certain aspects, the composition consists essentially of a lower alkyl acetate, an alcohol and water.

Also disclosed is a method of removing nail polish which comprises applying an effective amount of any one of the compositions and removing the nail polish. In certain embodiments, the nail polish is removed in less than a minute.

The formulation of a nail polish remover in accordance with this disclosure generally comprises (a) a solvent from the group of acetates; (b) an alcohol added as a diluent; (c) an alcohol to be used as an emulsifier to ensure the nail polish remover exists in one phase; and optionally (d) water. Further, the acetates can be butyl acetate and an isoamyl acetate mixture, and the alcohols can be ethyl alcohol and n-butanol.

As a solvent, n-butyl acetate has been shown to be effective at removing nail polish and other lacquers. It is made from the esterification of butanol and acetic acid, two compounds found in nature and made by various bacteria. This esterification can also be performed with isoamyl alcohol and acetic acid, thus forming isoamyl acetate and water. Isoamyl acetate is also effective in removing nail polish and other lacquers. This esterification can be performed over a reusable catalyst, thus reducing the use of sulfuric acid.

DETAILED DESCRIPTION OF THE INVENTION

Nail polish remover (NPR) formulations consist of the ingredients and concentrations listed in the table below:

| NPR Ranges and Exemplary Ranges | | |
|---|---|---|
| Range (v/v) | Compound | Exemplary range (v/v) |
| 0-30% | n-Butyl Acetate | 0-20% |
| 0-30% | Amyl Acetates Active Amyl Acetate Isoamyl Acetate | 0-20% |
| 0-70% | Ethyl Alcohol | 40-60% |
| 0-10% | Butanol | 0-5% |
| balance | Water and optional additives | balance |

An aspect of the formula preparation was a desire to prevent phase separation in the mixture. Different concentrations of the n-butyl acetate mixture, ethanol, and water were tested to see if phase separation occurred at certain times. The data is listed below:

| NPR Phase Separation Data | | | | | |
|---|---|---|---|---|---|
| % Concentration (v/v) | | | Phase Separation in: | | |
| NBuAc | EtOH | H$_2$O | immediately | 6 hrs | 24 hrs |
| 20 | 60 | 20 | No | No | No |
| 33.3 | 33.3 | 33.3 | Yes | Yes | Yes |
| 40 | 40 | 20 | No | No | |
| 10 | 45 | 45 | No, cloudy | No, cloudy | |
| 20 | 50 | 30 | No, cloudy | No, cloudy | |
| 43.5 | 43.5 | 13 | No | No | No |

In order to test the effectiveness of the nail polish remover, a sample glass plate was prepared by painting various nail polish samples on the surface. A cotton swab was then dipped in the nail polish remover and rubbed vigorously until all traces of the nail polish were removed from the plate. The amount of time required for each removal was measured.

The removal times in seconds for the nail polish samples are listed below in Table 1.

TABLE 1

Removal times of various nail polishes with the nail polish remover.

| Nail Polish Sample | Removal Time (seconds) |
|---|---|
| A | 10 |
| B | 5 |
| C | 5 |
| D | 3 |
| E | 4 |
| F | 5 |
| G | 5 |
| H | 5 |
| I | Little effect |
| J | 3 |
| K | 9 |
| L | 20 |

As it is shown, the nail polish remover was quite effective in removing all the samples with the exception of samples "I" and "L". Still, this table shows it removes most nail polishes rapidly (within 10 seconds) and effectively.

Further trials were performed on persons using one, two, and three coats of nail polish. These were performed as follows: testing with only nail polish, testing with a base coat and nail polish, testing with nail polish and a top coat, and testing with a base coat, nail polish and a top coat. Testing was also performed with and without using a quick set spray. These combinations were tested for removal after applications of one hour, three hours, one day, and one week. It was found that removal took the least amount of time for those nail polish samples without top coats. The top coats required five to ten seconds of soaking in the nail polish remover before they could be removed.

The formulations disclosed herein may be comprised entirely of components that are up to 100% renewable and from natural sources, decreasing the reliance on harmful petrochemicals.

Exemplary formulae comprise, consist essentially of, or consist of 0-30% n-Butyl Acetate (e.g., 0-20%), 0-30% amyl acetates (e.g., 0-20%), 0-70% Ethyl alcohol (e.g., 40-60%), 0-10% n-butanol (e.g., 0-5%) and 0-30% water (e.g., 10-25%).

Certain embodiments disclosed herein have an additional advantage over conventional nail polish removers by exhibiting antimicrobial activity. Concentrations of alcohol over 60% have been shown to be effective in destroying bacteria and other microorganisms (Rotter, 1999).

Nail polish remover concentrations of 100%, 75%, 50%, 25% and 0% diluted with water were deposited onto a plate plated with bacteria. After 24 hours, the plates with 100%, 75% and 50% concentrations of nail polish remover showed no growth, while the plates with 25% and 0% nail polish remover had no effect.

It is understood that the solution can contain small amounts of perfumes, dyes or other colorants, other additives (e.g., humectants such as glycerol) and the like, which do not interfere with nail polish removal. As such, the expression "consisting essentially of" is meant to encompass compositions containing ingredients that do not materially affect the nail polish removal property or quality.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. A nail polish remover composition which comprises:
a mixture of water and at least one lower alkyl acetate and an amount of at least one alcohol sufficient to emulsify the alkyl acetate to prevent phase separation of the mixture, the amounts of water, alkyl acetate and alcohol providing a combination of effective nail polish removal from a surface, resistance to phase separation, and resistance to turbidity, wherein the amount of water in the composition is less than 30% by volume, the amount of the at least one lower alkyl acetate is from 20% to 43.5% by volume, and the amount of the at least one alcohol is 40% to 60% by volume, wherein the at least one lower alkyl acetate is n-butyl acetate.

2. The composition of claim 1, further comprising an amyl acetate.

3. A nail polish remover composition which comprises:
a mixture of water and at least one lower alkyl acetate and an amount of at least one alcohol sufficient to emulsify the alkyl acetate to prevent phase separation of the mixture, the amounts of water, alkyl acetate and alcohol providing a combination of effective nail polish removal from a surface, resistance to phase separation, and resistance to turbidity, wherein the amount of water in the composition is less than 30% by volume, the amount of the at least one lower alkyl acetate is from 20% to 43.5% by volume, and the amount of the at least one alcohol is 40% to 60% by volume wherein the at least one alkyl acetate is isoamyl acetate.

4. The composition of claim 1, wherein the at least one alcohol contains 2 to 4 carbon atoms.

5. The composition of claim 4, wherein the at least one alcohol is ethanol.

6. The composition of claim 5, further comprising butyl alcohol.

7. A method of removing nail polish from a surface, comprising applying an effective amount of the composition of claim 1 to the surface, and removing the nail polish from the surface.

8. The method of claim 7, wherein the nail polish is removed in less than a minute.

* * * * *